United States Patent [19]

Howell

[11] Patent Number: 4,554,379

[45] Date of Patent: Nov. 19, 1985

[54] AMINOALKYL AROMATIC COMPOUNDS AND THEIR PRODUCTION

[75] Inventor: Frederick H. Howell, Atherton, England

[73] Assignee: Ciba Geigy Corporation, Ardsley, N.Y.

[21] Appl. No.: 724,494

[22] Filed: Apr. 18, 1985

Related U.S. Application Data

[63] Continuation of Ser. No. 663,263, Oct. 22, 1984, abandoned, which is a continuation of Ser. No. 609,517, May 11, 1984, abandoned, which is a continuation of Ser. No. 388,365, Jun. 14, 1982, abandoned.

[30] Foreign Application Priority Data

Jun. 19, 1981 [GB] United Kingdom ............... 8119008

[51] Int. Cl.$^4$ .................. C07C 91/16; C08G 69/26
[52] U.S. Cl. ..................... 564/374; 564/338; 564/378; 549/74; 528/335; 528/341; 528/346; 528/347
[58] Field of Search .................. 564/374, 338, 378

[56] References Cited

U.S. PATENT DOCUMENTS 2,900,369  8/1959  Edwards et al. ............... 564/374
4,130,579 12/1978  Frazer et al. ................. 564/374

Primary Examiner—Alan Siegel
Attorney, Agent, or Firm—Luther A. R. Hall

[57] ABSTRACT

New compounds having the formula:

$$R_4(QNH_2)_xI$$

wherein x is 1 or 2 and the residues $QNH_2$ are the same or different and each is a residue of formula:

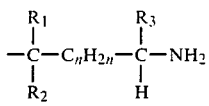

wherein n is an integer from 1 to 15, $R_1$ is $C_1$–$C_8$ alkyl, $R_2$ is $C_1$–$C_4$ alkyl or $R_1$ and $R_2$, together with the carbon atom to which they are attached, form a $C_5$–$C_8$ cycloalkylene residue, $R_3$ is H or $C_1$–$C_6$ alkyl, $C_3$–$C_8$ cycloalkyl or $C_6$–$C_{10}$ aryl and $R_4$ is a mono- or polyvalent $C_6$–$C_{20}$ aromatic or $C_4$–$C_{20}$ π-excessive heterocyclic residue; these compounds are useful as intermediates for polyamides, plastics and for compounds having biological activity.

5 Claims, No Drawings

AMINOALKYL AROMATIC COMPOUNDS AND THEIR PRODUCTION

This application is a continuation of application Ser. No. 663,263, filed Oct. 22, 1984, now abandoned which in turn is a continuation of application Ser. No. 609,517, filed May 11, 1984, now abandoned, which in turn is a continuation of Ser. No. 388,365, filed June 14, 1982, now abandoned.

The present invention relates to aminoalkyl aromatic compounds and a process for their production.

According to the present invention, there are provided compounds having the formula:

$$R_4(QNH_2)_x \qquad \qquad I$$

wherein x is 1 or 2 and the residues $QNH_2$ are the same or different and each is a residue of formula:

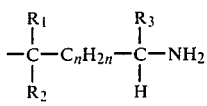

wherein n is an integer from 1 to 15, $R_1$ is $C_1$–$C_8$ alkyl, $R_2$ is $C_1$–$C_4$ alkyl or $R_1$ and $R_2$, together with the carbon atom to which they are attached, form a $C_5$–$C_8$ cycloalkylene residue, $R_3$ is H or $C_1$–$C_6$ alkyl, $C_3$–$C_8$ cycloalkyl or $C_6$–$C_{10}$ aryl and $R_4$ is a mono- or polyvalent $C_6$–$C_{20}$ aromatic or a $C_4$–$C_{20}$ $\pi$ excessive heterocyclic residue; as well as the corresponding salts of organic or inorganic acids.

Aromatic- or $\pi$-excessive heterocyclic residues $R_4$ may be mono-, di- or polynuclear systems. When the residues $R_4$ is a heterocyclic residue it may contain an oxygen, sulphur or $NR_5$ residue wherein $R_5$ is H or $C_1$–$C_4$ alkyl. When $R_4$ is a di- or polynuclear system, two or more aromatic- or $\pi$-excessive heterocyclic residues $R_4$ may be linked directly to one another via a single bond, via a saturated or unsaturated carbon chain containing from 1 to 4 carbon atoms, via an O or S atom, or an NH group, or the aromatic and/or $\pi$-excessive heterocyclic residues may be fused to form a polynuclear ring system. Aromatic or $\pi$-excessive heterocyclic residues $R_4$ may be optionally substituted by one or two $C_1$–$C_{12}$ alkyl groups, which may be the same or different, or by one or two halogen atoms which may be the same or different. Such halogen substituents may be F, Cl, Br or I atoms.

When $R_1$ is an alkyl group, it may be e.g. a methyl, ethyl, n-propyl, isopropyl, n-butyl, isobutyl, sec.-butyl, n-amyl, n-hexyl, hept-3-yl, or n-octyl group. When $R_2$ and/or $R_5$ is an alkyl group, it may be e.g. methyl, ethyl, n-propyl, isopropyl, n-butyl, isobutyl or sec.butyl. When $R_1$ and $R_2$, together with the carbon atom to which they are attached, form a cycloalkylene chain, this may be a cyclopentylene, cyclohexylene, cycloheptylene or cyclooctylene residue. When $R_3$ is an alkyl group, it may be e.g. a methyl, ethyl, n-propyl, isopropyl, n-butyl, sec.-butyl, amyl or hexyl group. Cycloalkyl groups $R_3$ may be e.g. cyclopropyl, cyclobutyl, cyclopentyl, cyclohexyl, cycloheptyl or cyclooctyl groups. When $R_3$ is an aryl group it may be a phenyl or naphthyl group. Mono- or polyvalent aromatic residues $R_4$ may be mono- or polyvalent benzene, chlorobenzene, toluene, xylene, isopropylbenzene, n-octylbenzene, diphenyl, diphenylether, diphenylsulphide, diphenylamine, diphenylmethane, diphenylethane, diphenylbutane, triphenylmethane, naphthalene, anthracene or phenanthrene residues. When $R_4$ is a $\pi$-excessive heterocyclic residue, it may be e.g. a thiophene, methylthiophene, pyrrole, furan, benzfuran, benzothiphene or indole residue.

Examples of salts of the compounds of formula I are the hydrochloride, hydrobromide, sulphate, phosphate, methansulphate, p-toluene sulphonate, formate, oxalate, adipate, benzoate and isophthalate salts.

Preferred compounds of formula I are those wherein $QNH_2$ has its previous significance, wherein n is 3 to 15, $R_1$ is $C_1$–$C_6$ alkyl, $R_2$ is $C_1$–$C_3$ alkyl, $R_3$ has its previous significance and $R_4$ is a mono- or divalent $C_6$–$C_{20}$ aromatic or $C_4$–$C_8$ $\pi$-excessive heterocyclic residue containing sulphur. More preferred compounds of formula I are those wherein x is 2, the residues $QNH_2$ are the same or different, more particularly the same, and have their previous significance, where n is 3 to 15, $R_1$ is $C_1$–$C_6$ alkyl, $R_2$ is $C_1$–$C_3$ alkyl, $R_3$ is H or $C_1$–$C_6$ alkyl and $R_4$ is 1,4-phenylene or

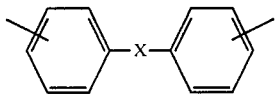

where X is a direct bond, $CH_2$, O, S or NH.

More preferred also are compounds of formula I wherein x is 1 and $QNH_2$ has its previous significance where n is 3 to 15, $R_1$ is $C_1$–$C_6$ alkyl, $R_2$ is $C_1$–$C_3$ alkyl, $R_3$ has its previous significance and $R_4$ is a monovalent $C_6$–$C_{20}$ aromatic or $C_4$–$C_8$ $\pi$-excessive heterocyclic residue.

Particularly preferred are compounds of formula I wherein x is 2, $QNH_2$ has its previous significance where n is 3 to 9, more particularly 3, 8 or 9, $R_1$ is $C_1$–$C_4$ alkyl, particularly methyl or ethyl, $R_2$ is methyl or ethyl particularly methyl, $R_3$ is $C_1$–$C_6$ alkyl, more particularly $C_1$–$C_4$ alkyl, and especially methyl or isopropyl, and $R_4$ is 1,4-phenylene or

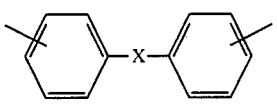

where X is a direct bond or, —O—, —CH$_2$—, or —NH—.

Examples of compounds of formula I include:
2-(6-Amino-2-methylhept-2-yl)thiophene
3-(6-Amino-2-methylhept-2-yl)thiophene
2,4-bis-(6-Amino-2-methylhept-2-yl)thiophene
2,5-bis-(6-Amino-2-methylhept-2-yl)thiophene
2-Amino-6-methyl-6-phenylheptane
1,4-bis-(6-Amino-2-methylhept-2-yl)benzene
Bis-1,4-(12-amino-3,13-dimethyltetradec-3-yl)-benzene
Bis-1,4-(12-amino-2,13-dimethyltetradec-2-yl)-benzene
1-(12-Amino-3,13-dimethyltetradec-3-yl)-4-(12-amino-2,13-dimethyltetradec-2-yl)-benzene
2-Amino-6-(3,4-dimethylphenyl)-6-methylheptane
2-Amino-6-(4-isopropylphenyl)-6-methylheptane
2-Amino-6-(4-n-octylphenyl)-6-methylheptane
3-Amino-12-(3,4-dimethylphenyl)-12-methyltetradecane
3-Amino-13-(3,4-dimethylphenyl)-13-methyltetradecane 4,4'-bis-(6-Amino-2-methylhept-2-yl)diphenyl
4,4'-bis-(6-Amino-2-methylhept-2-yl)diphenylmethane
4-(6-Amino-2-methylhept-2-yl)diphenylether
4,4'-bis-(6-Amino-2-methylhept-2-yl)diphenylether
4-(6-amino-2-methylhept-2-yl)-4'-(12-amino-2,13-dimethyltetradec-2-yl)diphenylether
4,4'-bis-(2-Amino-6-methylhept-2-yl)diphenylsulphide
4,4'-bis-(6-Amino-2-methylhept-2-yl)diphenylamine
2,6-bis-(6-Amino-2-methylhept-2-yl)naphthalene
2,7-bis-6-Amino-2-methylhept-2-yl)naphthalene
2-Amino-6-methyl-6-(4-chlorophenyl)heptane
4,4'-bis-(6-Amino-2-methylhept-2-yl)-1,2-diphenylethane
4,4'-bis-(6-Amino-2-methylhept-2-yl)-1,1-diphenylethane
2,6-bis-(6-Amino-2-methylhept-2-yl)-anthracene
4,4'-bis-(6-Amino-2-methylhept-2-yl)-triphenylmethane
3,9-bis-(6-Amino-2-methylhept-2-yl)-phenanthrene
3,10-bis-(6-Amino-2-methylhept-2-yl)-phenanthrene.

Preferred compounds of formula I are:
Mixtures of 2,4- and 2,5-bis-(6-amino-2-methylhept-2-yl)thiophene,
1,4-Bis-(6-amino-2-methylhept-2-yl)benzene,
2-Amino-6-(3,4-dimethylphenyl)-6-methylheptane,
2-Amino-6-(4-isopropylphenyl)-6-methylheptane,
6-(4-n-Octylphenyl)-6-methyl-2-heptylamine.
Mixtures of 3-amino-12-(3,4-dimethylphenyl)-12-methyltetradecane and 3-amino-13-(3,4-dimethylphenyl)-13-methyl-tetradecane,
4,4'-Bis-(6-amino-2-methylhept-2-yl)diphenyl,
4-(6-Amino-2-methylhept-2-yl)diphenyl ether,
Bis-(6-amino-2-methylhept-2-yl)diphenyl ether,
Bis(6-amino-2-methylhept-2-yl)diphenyl methane,
4,4'-Bis-(6-amino-2-methylhept-2-yl)diphenylamine.

The present invention also provides a process of producing a compound of formula I comprising reacting, at a temperature in the range of from 0° to 150° C., preferably from 15°–110° C., in the presence of a Friedel-Crafts catalyst, a compound of formula:

$$R_4Z_x \qquad \text{II}$$

wherein $R_4$ and x have their previous significance and Z is a replaceable hydrogen atom, with at least x moles of a compound (III) which is an amino-alcohol or amino-olefin, or salt thereof with an organic or inorganic acid, capable of replacing an H atom in the compound of formula II by a group of formula:

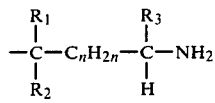

Preferably, the compound(III) is an amino alcohol, or a salt thereof with an organic or inorganic acid and is capable of providing, or of being converted into a residue of formula IV. If more than one group of formula IV is introduced into the compound of formula II, then up to two groups of formula IV may be present per aromatic or π-excessive heterocyclic nucleus in the compound of formula II providing that the compound of formula I so produced does not contain more than two groups of formula IV. When two groups of formula IV are introduced into the compound of formula II, these groups may be the same or different and, if desired, they may be introduced stepwise.

The reaction catalyst may be a Brönsted acid or Lewis acid. Brönsted acids suitable for this purpose are sulphuric acid, phosphoric acid or hydrochlorid acid; preferred Lewis acids are metal halides, e.g. $ZnCl_2$, $SnCl_4$ or $FeCl_3$ and especially $AlCl_3$.

The reaction is conveniently effected under conditions of ambient temperature and pressure and in the presence of an inert solvent, the nature of which will depend on the type of the catalyst used.

For reactions using Brönsted acids, non-reactive solvents such as alcohols and water may be used as diluents. Sulphuric acid, for example, may be used in conjunction with methanol or water, and hydrogen chloride may be used in aqueous solution. Lewis acids such as $AlCl_3$ are suitably employed with nitro-methane and chlorinated hydrocarbons.

After completion of the alkylation, the aminoalkyl-aromatic product may be freed from Brönsted or Lewis acid catalyst by treatment with aqueous base. Suitable bases for this purpose are alkali metal hydroxides or ammonia. The preferred bases are sodium and ammonium hydroxide. Following liberation of the aminoalkylaromatic, it may be separated from the aqueous phase with a non miscible organic solvent such as ether, and then, following water washing, the final product may be obtained by distillation under reduced pressure.

Examples of aromatic reactants of formula $R_4Z_x$ may be divided into the following three categories:

(1) Mononuclear aromatics and π-excessive heterocycles

This group includes benzene, alkyl and halogen substituted benzenes, monocyclic heterocycles, and alkyl substituted monocyclic heterocycles. Examples of such compounds are: benzene, toluene, ethylbenzene, n-propylbenzene, cumene, n-butylbenzene, sec-butylbenzene, tert-butylbenzene, n-octylbenzene, t-octylbenzene, o-xylene, chlorobenzene, thiophene, 2-methylthiophene, 3-methylthiophene.

(2) Linked Aromatics

One or more aryl groups are linked together directly by a single bond or through another atom or atoms which may be carbon ($C_1$–$C_4$), oxygen, sulphur or nitrogen. Examples of such compounds are: diphenyl, terphenyl, diphenylmethane, 1,2-diphenylethane, 1,1-diphenylethane, triphenylmethane, diphenylether, diphenylsulphide, diphenylamine.

(3) Fused ring aromatics and π-excessive heterocyclics

Two or more aromatic residues which share adjacent carbon atoms are fused to form di- and polynuclear aromatics or π-excessive heterocyclics. The fused aromatic system may be further substituted by one or more alkyl ($C_1$–$C_4$) or by halogen.

Examples of such compounds are: naphthalene, 1-methylnaphthalene, 2-methylnaphthalene, 1-chloronaphthalene, 2-chloronaphthalene, 1,3-dimethylnaphthalene, 1,4-dimethylnaphthalene, 1,5-dimethylnaphthalene, 2,3-dimethylnaphthalene, dimethylnaphthalene mixed isomers, anthracene, phenanthrene, benzthiophene.

Compounds III capable of introducing a group of formula IV into the molecule of the aromatic system of formula $R_4Z_x$, include those having the formula:

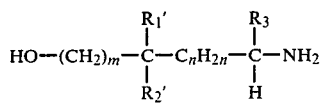

wherein R₃ has its previous significance and, when m is 0, n is 1 to 15, $R_1'$ is $C_1$–$C_8$ alkyl, $R_2'$ is $C_1$–$C_4$ alkyl, or $R_1'$ and $R_2'$, together with the carbon atom to which they are attached, form a $C_5$–$C_8$ cycloalkylene residue and, when m is 1, n is 1 to 14, $R_1'$ is $C_1$–$C_7$ alkyl, $R_2'$ is H or $C_1$–$C_3$ alkyl or $R_1'$ and $R_2'$, together with the carbon atom to which they are attached, form a $C_5$–$C_7$ cycloalkylene residue.

When m is 1 in the compounds of formula IVa, the methylene group $(CH_2)_m$ is caused to insert into one of the groups $R_1'$, $R_2'$ or $-C_nH_{2n}-$ thereby increasing by one the carbon number of that group.

Examples of compounds of formula IVa include those wherein m=0, n=3 and $R_1'$, $R_2'$ and $R_3$ are each methyl; m=0, n=8, 1 $R_1'$ and $R_2'$ are each methyl and $R_3$ is isopropyl; and m=1, n=8 and $R_1'$, $R_2'$ and $R_3$ are as follows:

| $R_1'$ | $R_2'$ | $R_3$ |
|---|---|---|
| CH₃ | CH₃ | $C_2H_5$; |
| CH₃ | CH₃ | $C_3H_7$ |
| $C_3H_7$ | $C_3H_7$ | CH₃ |
| $C_2H_5$ | $C_2H_5$ | $C_4H_9$ |
| $C_2H_5$\CH—/$C_4H_9$ | $C_2H_5$ | $C_4H_9$ |
| $-(CH_2)_5-$ | | $C_2H_5$ |
| $C_2H_5$ | $C_2H_5$ | $(C_2H_5)_2CH-$ |
| CH₃ | H | $C_6H_5$ |

Suitable amino-alcohols for use as compound III may be selected from appropriate 11-amino-undecanols having the formula:

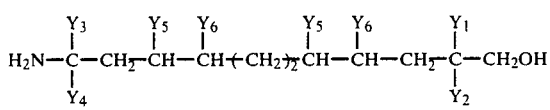

wherein $Y_1$ and $Y_3$, independently, are H or $C_1$–$C_8$ alkyl; $Y_2$ and $Y_4$, independently, are $C_1$–$C_8$ alkyl; or $Y_1$ and $Y_2$ and/or $Y_3$ and $Y_4$, together with the C atoms to which they are bonded, form $C_4$–$C_8$ cycloaliphatic ring; and $Y_5$ and $Y_6$, independently, are H or $C_1$–$C_4$ alkyl.

These 11-amino-undecanols are described in more detail, together with their method of manufacture in German Offenlegungsschrift No. 2831299.

Especially preferred are heptaminol(2-amino-6-hydroxy-6-methyl-heptane) and 11-amino-2,2,12-trimethyl-tridecan-1-ol.

Amino-olefins III capable of introducing a group of formula IV into the molecule of the aromatic system of formula $R_4Z_x$ include 2-amino-6-methyl-hept-5-ene and 2-amino-6-methyl-hept-6-ene and olefins formed by dehydration of the above-described amino-alcohols.

The substitution pattern of aromatic systems by the alkylamino group is directly dependent on the aromatic system itself.

In certain aromatic systems, alkylation leads to a single isomer while for others, mixtures isomers are formed.

For example the monoalkylation of o-xylene leads exclusively to substitution in the 4-position while for cumene and n-octylbenzene, alkylation proceeds to give mainly the 4-substitution product.

Where dialkylation occurs, aromatics such as benzene and diphenyl, give 1,4 and 4,4', substitution respectively, while for aromatics such as naphthalene, diphenylmethane, diphenylether, and thiophene two or more substitution isomers are produced. Diphenylamine gives the 4,4'-disubstituted product.

The compounds of the invention are useful as intermediates for polyamides, plastics and for compounds with biological activity.

Preferred compounds of Formula I for use as intermediates in the preparation of polyamides are those wherein x is 2, and the residues $QNH_2$, which are the same or different, more particularly the same, have their previous significance, where n is 3 to 15, $R_1$ is $C_1$–$C_6$ alkyl, $R_2$ is $C_1$–$C_3$ alkyl, $R_3$ is H or $C_1$–$C_6$ alkyl, and $R_4$ is 1,4-phenylene, or a group of formula:

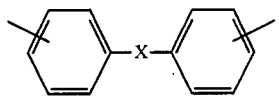

where X is a direct bond, $-CH_2-$, $-O-$, $-S-$, or $-NH-$. More preferred for this use are compounds of formula I wherein x is 2, the residues $QNH_2$ have their previous significance where n is 3 to 9, more particularly 3, 8 or 9, $R_1$ is $C_1$–$C_4$ alkyl, $R_2$ is methyl or ethyl, $R_3$ is $C_1$–$C_6$ alkyl, more particularly $C_1$–$C_4$ alkyl and especially methyl or isopropyl $R_4$ is 1,4-phenylene or a group of formula:

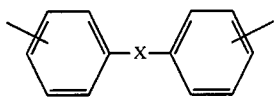

where X is a direct bond or $-O-$, $-CH_2-$ or $-NH-$.

The new transparent polyamides prepared from the compounds of formula I are distinguished by improved thermoplastic processing characteristics, are resistant to boiling water and have a low water absorption, high stability to hydrolysis, good dimentional stability under the action of moisture, and correspondingly improved and electrical properties.

They have reduced specific viscosity of at least 0.3 dl/g, preferably about 0.5 to about 2.0 dl/g, and particularly about 0.7 to about 1.8 dl/g, measured on a 0.5% solution in m-cresol at 25° C., and they consist of recurring structural elements of formula VI

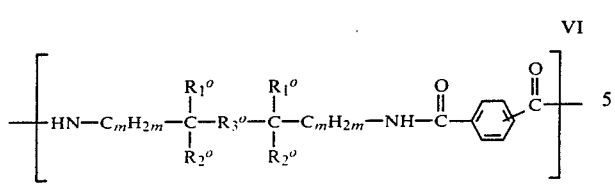

wherein the two m independently of each other are an integer of from 4 to 16, the two $R_1°$ independently of each other are $C_{1-6}$ alkyl, the two $R_2°$ independently of each other are $C_{1-3}$ alkyl and $R_3°$ is 1,4-phenylene or

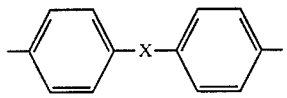

wherein X is the direct bond, $-CH_2-$, $-O-$, $-S-$ or $-NH-$, and whereby the carbonyl groups are linked to the benzene ring in 1,3- and/or 1,4-position.

Preferably, the two m have the same meaning, the two $R_1°$ represent identical alkyl groups and the two $R_2°$ each represent the same alkyl group.

Preferred compounds of formula I for use as intermediates for compounds with biological activity are those wherein x is 1 and $QNH_2$ has its previous significance where n is 3 to 15, $R_1$ is $C_1-C_6$ alkyl, $R_2$ is $C_1-C_3$ alkyl, $R_3$ is H, $C_1-C_6$ alkyl, $C_3-C_8$ cycloalkyl or $C_6-C_{10}$ aryl and $R_4$ is a monovalent $C_6-C_{20}$ aromatic or $C_4-C_8$ π-excessive heterocyclic residue.

The following Examples further illustrate the present invention. Parts and percentages shown therein are by weight unless otherwise stated. Pressures shown therein are expressed in millibars.

EXAMPLES

Example 1

To 4.2 parts of thiophene and 18.2 parts of 6-hydroxy-6-methyl-2-heptylamine hydrochloride (heptaminol hydrochloride) in 50 parts of nitromethane were added 26.7 parts of aluminiumchloride in 50 parts nitromethane at room temperature. The homogeneous solution, after storage at room temperature for a further two days, was poured into water and treated with caustic soda solution until the aqueous phase was alkaline. The organic phase was ether extracted, washed with water, evaporated and distilled to give a mixture of 2,4 and 2,5-bis-(6-amino-2-methylhept-2-yl)thiophene $b_{0.8}$ 174°–80° with the following percentage composition by weight.

|  | C | H | N |
|---|---|---|---|
| Found | 70.76 | 11.68 | 7.93% |
| Calculated for $C_{20}H_{38}N_2S$ | 70.96 | 11.31 | 8.27% |

Example 2

To a stirred solution of 256 parts 98% w/w sulphuric acid, 48 parts of methanol, and 7.8 parts of benzene, there was added at room temperature, 36.0 parts of heptaminol hydrochloride in 3.0 part lots every 6 hours. After the final addition at 66 hours, the reaction mixture was stirred a further 18 hours at room temperature and then diluted with water. The aqueous solution was then neutralised with sodium hydroxide solution and the organic phase ether extracted, washed with water, evaporated, and distilled to give 18.7 parts of 1,4-bis-(6-amino-2-methylhept-2-yl)benzene, $b_{0.8}$ 180°–90° with the following percentage composition by weight.

|  | C | H | N |
|---|---|---|---|
| Found | 79.45 | 12.24 | 9.01% |
| Calculated for $C_{22}H_{40}N_2$ | 79.45 | 12.12 | 8.42% |

Example 3

21.2 Parts of o-xylene, 128 parts of 98% w/w sulphuric acid, 24 parts of methanol, and 36.3 parts of heptaminol hydrochloride were stirred at room temperature for 3 days. The work up was carried out as described in Example 2 and gave on distillation 36.2 parts of 2-amino-6-(3,4-dimethylphenyl)-6-methylheptane $b_{16}$ 164°–8° with the following percentage composition by weight.

|  | C | H | N |
|---|---|---|---|
| Found | 82.94 | 12.05 | 6.06% |
| Calculated for $C_{16}H_{27}N$ | 82.34 | 11.66 | 6.00% |

Example 4

Example 3 was repeated using 24 parts of cumene in place of o-xylene. Distillation gave 27.1 parts 2-amino-6-(4-isopropylphenyl)-6-methylheptane $b_{16}$ 172°–6° with the following percentage composition by weight.

|  | C | H | N |
|---|---|---|---|
| Found | 81.92 | 11.57 | 5.98% |
| Calculated for $C_{17}H_{29}N$ | 82.53 | 11.81 | 5.66% |

Example 5

6-(4-n-Octylphenyl)-6-methyl-2-heptylamine $b_{0.26}$ 162°–6° was prepared following the procedure of Example 3 from n-octylbenzene and heptaminol hydrochloride.

Example 6

10.2 Parts of o-xylene, 128 parts of 98% w/w sulphuric acid, 24 parts of methanol, and 12.8 parts of 11-amino-2,2-dimethyltridecan-1-ol were reacted together and worked up according to Example 3. Distillation gave an isomeric mixture of 12.1 parts of 3-amino-12-(3,4-dimethylphenyl)-12-methyl-tetracecane and 3-amino-13-(3,4-dimethylphenyl)-13-methyl-tetradecane, $b_{0.3}$ 166°–9°, having the following percentage composition by weight:

|  | C | H | N |
|---|---|---|---|
| Found | 82.69 | 12.47 | 4.72 |
| Calculated for $C_{23}H_{41}N$ | 83.31 | 12.46 | 4.22 |

Example 7

15.4 Parts of diphenyl were reacted with 42.0 parts of heptaminol hydrochloride according to the procedure of Example 2. Distillation gave 29.0 parts of 4,4'-bis-(6- amino-2-methylhept-2-yl)diphenyl $b_{0.3}$ 220°–235° with the following percentage composition by weight.

|  | C | H | N |
| --- | --- | --- | --- |
| Found | 81.77 | 11.04 | 6.84% |
| Calculated for $C_{28}H_{44}N_2$ | 82.29 | 10.85 | 6.85% |

Example 8

To 8.5 parts of diphenylether and 26.7 parts aluminum chloride in 50 parts nitromethane, were added 18.2 parts of heptaminol hydrochloride portionwise. After the addition, the reaction mixture was stored for 3 days at room temperature and then worked up according to the procedure of Example 1. Distillation gave 2.1 parts of 4-(6-amino-2-methylhept-2-yl)diphenylether $b_{0.4}$ 170°–80° followed by 14.2 parts of bis-(6-amino-2-methylhept-2-yl)diphenylether $b_{0.7}$ 240°–70°. Analysis of this second fraction showed it to contain 70% of the 4,4′-isomer. The percentage compositions of fractions 1 and 2 were respectively:

|  | C | H | N |
| --- | --- | --- | --- |
| Found | 80.38 | 9.74 | 5.28% |
| Calculated for $C_{20}H_{27}NO$ | 80.76 | 9.15 | 4.71% |
| Found | 79.31 | 10.61 | 6.72% |
| Calculated for $C_{28}H_{44}N_2O$ | 79.19 | 10.44 | 6.60% |

Example 9

16.8 parts of diphenylmethane were reacted with 36.4 parts of heptaminol hydrochloride according to the procedure of Example 2. Distillation gave 22.4 parts of bis-(6-amino-2-methylhept-2-yl)diphenylmethane $b_{0.4}$ 230°–44° C. Analysis of this fraction showed it to contain 73% of the 4,4′-isomer with the following percentage composition by weight

|  | C | H | N |
| --- | --- | --- | --- |
| Found | 82.71 | 11.31 | 6.55 |
| Calculated for $C_{29}H_{46}N_2$ | 82.40 | 10.97 | 6.63 |

Example 10

16.9 parts of diphenylamine, 20.4 parts of 36% w/w aqueous hydrochloric acid, 6.8 parts of anhydrous zinc chloride, 36.4 parts of heptaminol hydrochloride and 20 parts of water were stirred and refluxed for 4 days. On cooling, the reaction mixture was treated with 50 parts sodium hydroxide in 100 parts of water and the organic phase ether extracted, washed with water, evaporated and distilled. After removing 8.0 parts of a first fraction $b_{0.33}$ 146°–238°, 29.6 parts of 4,4′-bis-(6-amino-2-methylhept-2-yl)diphenylamine $b_{0.3}$ 254°–58° was obtained (70% yield) with the following percentage composition by weight.

|  | Carbon | Hydrogen | Nitrogen |
| --- | --- | --- | --- |
| Found | 79.59 | 10.93 | 9.84 |
| Calculated for $C_{28}H_{45}N_3$ | 79.37 | 10.70 | 9.91 |

Example 11

To 53.4 parts of aluminium chloride and 80 parts of benzene dissolved in 200 parts of nitromethane were added 36.4 parts of 6-hydroxy-6-methyl-3-heptylamine hydrochloride over 1 hour. After storage overnight at room temperature, the reaction mixture was poured into 400 parts of water, and 46% w/w sodium hydroxide solution added until the precipitated aluminium hydroxide had dissolved. The organic phase was ether extracted, washed with water, evaporated, and distilled to give 14.2 parts of 2-amino-6-methyl-6-phenylheptane $b_{0.1}$ 110° C. with the following percentage composition by weight.

|  | C | H | N |
| --- | --- | --- | --- |
| Found | 80.70 | 11.46 | 6.81 |
| Calculated for $C_{14}H_{23}N$ | 81.89 | 11.29 | 6.82 |

Example 12

In a flask fitted with stirrer, reflux condenser and dropping funnel 2.556 g (0.0154 moles) of terephthalic acid are slurried in 100 ml of 50% w/w ethanol and heated to reflux temperature. There are then introduced into the boiling reaction mixture from the dropping funnel 5.137 g (0.0154 moles) of the product of Example 2, 1,4-bis-(6-amino-2-methylhept-2-yl)-benzene. A clear solution is formed from which, after a few minutes, the salt which has formed precipitates. The salt is filtered off and dried at 80° C. in vacuo. Yield 6.5 g (85% of theory).

The salt is then introduced into a bomb tube fitted with a screw cover and with an incorporated pressure relief valve. After the air in the bomb has been completely expelled by nitrogen, the bomb tube is closed. It is then immersed into a salt bath having a temperature of 270° C. A clear melt has formed after a short time. After two hours the reaction is interrupted by removing the tube from the salt bath and releasing the excess pressure by opening the valve. The precondensate, which has solidified, is removed from the tube and transferred to a condensation vessel. With the strict exclusion of air and the continuous passing through of nitrogen, the melt which has formed is polycondensed at 280°. The water which forms during the polycondensation is continuously removed by the flow of nitrogen. After 5 hours the polycondensation is interrupted. On cooling, the melt solidifies into a transparent colourless mass.

2 to 3 g of the polyamide thus obtained are then moulded into an about 0.3 to 0.5 mm thick sheet by means of a heatable hydraulic press. The sheet is exposed at room temperature to a relative humidity of 65% until no further increase in weight can be detected. The reduced viscosity of the polyamide is measured on a 0.5% solution in m-cresol at 25° C. and is 1.13 dl/g; its glass transition temperature is determined in a differential calorimeter (DSC) and is 135° C.

What we claim is:

1. A compound having the formula I $$R_4(QNH_2)_x \qquad (I)$$

wherein x is 2 and the residues QNH₂ are the same or different and each is:

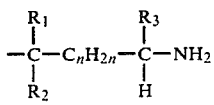

wherein n is an integer from 1 to 15, $R_1$ is $C_1$–$C_8$ alkyl, $R_2$ is $C_1$–$C_4$ alkyl or $R_1$ and $R_2$, together with the carbon atom to which they are attached, form a $C_5$–$C_8$ cycloalkylene residue, $R_3$ is $C_1$–$C_6$ alkyl, $C_3$–$C_8$ cycloalkyl or $C_6$–$C_{10}$ aryl and $R_4$ is a polyvalent mononuclear $C_6$–$C_{20}$ aromatic residue; as well as the corresponding salts of organic or inorganic acids.

2. A compound of formula I according to claim 1, wherein the residue $QNH_2$ is as defined in claim 1 wherein n is 3 to 15, $R_1$ is $C_1$–$C_6$ alkyl, $R_2$ is $C_1$–$C_3$ alkyl, $R_3$ is as defined in claim 1 and $R_4$ is a divalent mononuclear $C_6$–$C_{20}$ aromatic residue.

3. A compound of formula I according to claim 1, wherein x is 2, the residue $QNH_2$ is as defined in claim 1 and wherein n is 3 to 15, $R_1$ is $C_1$–$C_6$ alkyl, $R_2$ is $C_1$–$C_3$ alkyl, $R_3$ is $C_1$–$C_6$ alkyl and $R_4$ is 1,4-phenylene.

4. A compound according to claim 1, which is 1,4-bis-(6-amino-2-methylhept-2-yl)benzene.

5. A compound of formula I according to claim 1 wherein x is 2, the residue $QNH_2$ is as defined in claim 1, and wherein n is 3 to 9, $R_1$ is $C_1$–$C_4$ alkyl, $R_2$ is methyl or ethyl, $R_3$ is $C_1$–$C_6$ alkyl and $R_4$ is 1,4-phenylene.

* * * * *